Figure 1A:
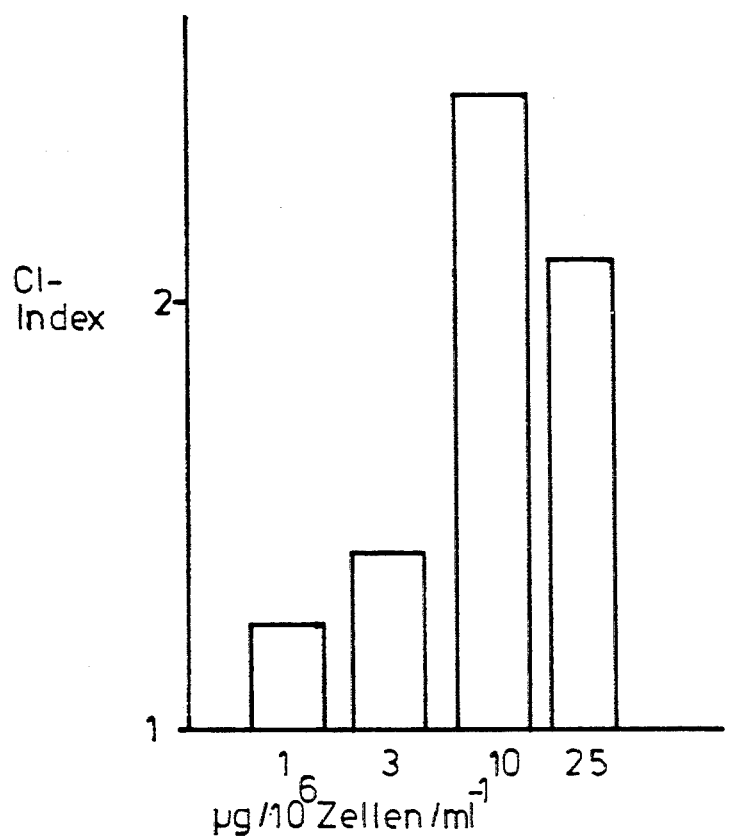

United States Patent [19]

Lockhoff et al.

[11] Patent Number: 5,070,190
[45] Date of Patent: Dec. 3, 1991

[54] SUBSTITUTED N-GLYCOSYLAMIDES, PROCESS FOR THEIR PREPARATION, AND THEIR USE AS MEDICAMENTS

[75] Inventors: Oswald Lockhoff, Cologne; John Goossens, Leverkusen; Helmut Brunner, Wuppertal; Michael Sperzel, Wuppertal; Klaus G. Stünkel, Wuppertal, all of Fed. Rep. of Germany

[73] Assignee: Bayer Aktiengesellschaft, Leverkusen, Fed. Rep. of Germany

[21] Appl. No.: 336,497

[22] Filed: Apr. 12, 1989

[30] Foreign Application Priority Data

Apr. 16, 1988 [DE] Fed. Rep. of Germany ....... 3812681

[51] Int. Cl.$^5$ .......................... A61K 31/70; C07H 5/04
[52] U.S. Cl. ...................................... 536/22; 536/18.7; 514/885; 530/322
[58] Field of Search ................. 536/18.7, 22; 514/885, 514/8, 42; 530/322

[56] References Cited

U.S. PATENT DOCUMENTS

| | | | |
|---|---|---|---|
| 4,574,122 | 3/1986 | Krüger et al. | 514/42 |
| 4,683,222 | 7/1987 | Stadler et al. | 514/42 |
| 4,686,208 | 8/1987 | Lockhoff et al. | 514/42 |
| 4,699,899 | 10/1987 | KLrüger et al. | 514/42 |
| 4,710,491 | 12/1987 | Lockhoff et al. | 514/42 |
| 4,716,152 | 12/1987 | Krüger et al. | 514/25 |
| 4,737,488 | 4/1988 | Lockhoff et al. | 514/42 |
| 4,855,283 | 8/1989 | Lockhoff et al. | 514/8 |
| 4,866,035 | 9/1989 | Durette | 514/42 |
| 4,868,157 | 9/1989 | Durette | 514/42 |
| 4,891,425 | 1/1990 | Lockhoff et al. | 536/22 |

*Primary Examiner*—Ronald W. Griffin
*Attorney, Agent, or Firm*—Sprung Horn Kramer & Woods

[57] ABSTRACT

The invention relates to new N-glycosylamides of the general formula I

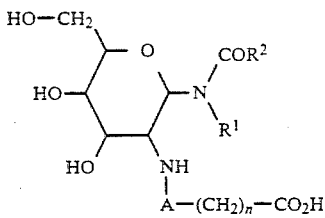

in which $R^1$ denotes a saturated alkyl radical or a singly, doubly or triply unsaturated alkenyl radical having up to 50 carbon atoms, $R^2$ denotes a saturated alkyl radical or a singly, doubly or triply unsaturated alkenyl radical having up to 50 carbon atoms, A represents —CO— or represents a group

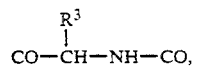

in which $R^3$ represents hydrogen, $C_1$–$C_7$alkyl, hydroxymethyl, 1-hydroxyethyl, mercaptomethyl, 2-methylthioethyl, 3-aminopropyl, 2-ureidopropyl, 3-guanidylpropyl, 4-aminobutyl, carboxymethyl, carbamoylmethyl, 2-carboxyethyl, 2-carbamoylethyl, benzyl, 4-hydroxybenzyl, 3-indolylmethyl or 4-imidazolylmethyl, and n represents 0 to 10, and which are substituted in the sugar residue with an amino acid residue, as well as process for their preparation and their use as medicaments.

9 Claims, 1 Drawing Sheet

SUBSTITUTED N-GLYCOSYLAMIDES, PROCESS FOR THEIR PREPARATION, AND THEIR USE AS MEDICAMENTS

The invention relates to new N-glycosylamides which are substituted in the sugar residue with an amino acid residue, as well as to process for their preparation and their use as medicaments.

It has already been disclosed that the class of compounds comprising N-glycosylamides, N-glycosylureas and N-glycosylcarbamates which are substituted in the sugar residue with an amino acid increase the antibody synthesis of the immune system on stimulation with an antigen and, furthermore, non-specifically enhance the host's intrinsic defences.

Details of the chemistry as well as of the action of these compounds are described in German Offenlegungsschrift A 2,206,037 as well as in European Published Specification B 1,091,645.

However, a disadvantage of the compounds described therein is that they are hydrophobic and thus it is virtually impossible to formulate them in water alone.

Attempts to improve the solubility in water by chemical derivatizations has hitherto always resulted in a reduction in the action.

It has now been found, surprisingly, that the compounds mentioned hereinafter are readily soluble in water while retaining the action.

The new compounds correspond to the general formula I

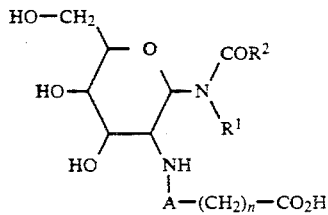

in which $R^1$ denotes a saturated alkyl radical or a singly, doubly or triply unsaturated alkenyl radical having up to 50 carbon atoms, $R^2$ denotes a saturated alkyl radical or a singly, doubly or triply unsaturated alkenyl radical having up to 50 carbon atoms, A represents —CO— or represents a group

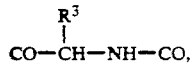

in which $R^3$ represents hydrogen, $C_1$-$C_7$-alkyl, hydroxymethyl, 1-hydroxyethyl, mercaptomethyl, 2-methylthioethyl, 3-aminopropyl, 3-ureidopropyl, 3-guanidylpropyl, 4-aminobutyl, carboxymethyl, carbamoylmethyl, 2-carboxyethyl, 2-carbamoylethyl, benzyl, 4-hydroxybenzyl, 3-indolylmethyl or 4-imidazolylmethyl, and n represents 0 to 10.

$R^1$ and $R^2$ preferably represent a straight-chain or branched saturated alkyl radical or a singly, doubly or triply unsaturated alkenyl radical having up to 30 carbon atoms. $R^1$ and $R^2$ particularly preferably represent a radical having 8 to 20 carbon atoms.

Particularly preferred examples of alkyl radicals in $R^1$ or $R^2$ are decyl, undecyl, dodecyl, tridecyl, tetradecyl, pentadecyl, hexadecyl, heptadecyl, octadecyl, nonadecyl and eicosyl.

Examples of the particularly preferred unsaturated alkenyl radicals of $R^1$ and $R^2$ are decenyl, undeceyl, dodecenyl, tridecenyl, tetradecenyl, pentadecenyl, hexadecenyl, heptadecenyl, octadecenyl, nonadecenyl and eicosenyl.

The radicals $R^1$ can also be branched, saturated alkyl chains or singly or doubly unsaturated alkenyl chains. The alkyl radicals particularly preferred in this connection as alkyl substituents are those which have up to 12 carbon atoms.

The radical $R^2$ preferably represents a straight-chain or branched, saturated or singly, doubly or triply unsaturated alkyl radical having up to 30 carbon atoms, particularly preferably having 8 to 20 carbon atoms.

The preferred representations of $R^3$ are hydrogen, $C_1$-$C_7$-alkyl, hydroxymethyl, 1-hydroxyethyl, carboxymethyl, 2-carboxyethyl, benzyl and 4-hydroxybenzyl.

$R^3$ particularly preferably represents hydrogen or $C_1$-$C_7$-alkyl.

The scope of the invention also embraces salts of the compounds of the formula I. These principally take the form of non-toxic salts, which can normally be used in pharmacy, or of compounds of the formula I. These salts are obtainable by reaction with suitable bases. Examples of these are ethanolmine, ethylenediamine, ammonia, choline, calcium, dicyclohexylamine, diisopropylamine, potassium, magnesium, N-methylglucamine, sodium, morpholine, piperazine, piperidine or tris(hydroxymethyl)aminomethane.

As is evident from formula I, the compounds according to the invention are derived from a substituted 2-amino-2-deoxyhexose as basic structure. These sugars are always connected N-glycosidically via the anomeric carbon atom to the alkylamido group having the abovementioned meanings for $R^1$ and $R^2$.

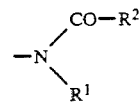

Preferred aminosugars in the compounds of the formula I according to the invention are 2-amino-2-deoxy-D-glucose and 2-amino-2-deoxy-D-galactose.

The 2-amino group in the said aminosugars in the compounds of the formula I according to the invention is connected either amidically to an acid radical —CO—$(CH_2)_n$—$CO_2H$ $CO_2H$ or amidically to an α-acylamino carboxylic acid derivative.

Preferred amino acids are the natural L-amino acids such as glycine, sarcosine, hippuric acid, alanine, valine, leucine, isoleucine, serine, threonine, cysteine, methionine, ornithine, citrulline, arginine, aspartic acid, asparagine, glutaric acid, glutamine, phenylalanine, tyrosine, proline, tryptophan and histidine. The D isomers of the said amino acids can likewise function as substituents.

The N-glycosylamides according to the invention, of the general formula (I), can be prepared by reacting glycosylamides of the general formula (II)

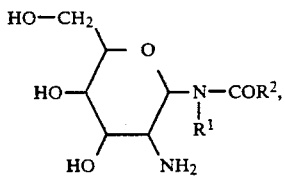

in which

R¹ and R² have the abovementioned meaning, or peptidoglycolipids of the general formula (III)

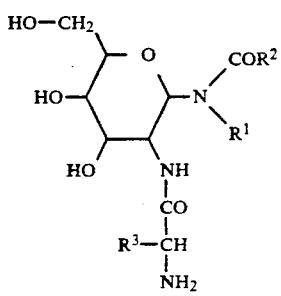

in which

R¹, R² and R³ have the abovementioned meaning, by known methods with dicarboxylic acid derivatives, which are activated where appropriate, with the amino group being converted into an amido group.

In variant A, compounds of the general formula (II) or (III) are reacted either with a non-activated dicarboxylic acid or a derivative of the dicarboxylic acid in the presence of a condensing agent or else with an activated dicarboxylic acid derivative without the presence of a condensing agent. The dicarboxylic acid derivatives which can be used in this variant A are represented by the general formula (IV)

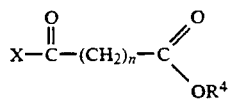

in which $R^4$ represents hydrogen, $C_1$-$C_7$-alkyl, aralkyl or an aralkyl radical which is optionally substituted in the ring, and X represents hydroxyl, alkyloxy, halogen, alkylcarbonyloxy, alkyloxycarbonyloxy or an activating radical known from peptide chemistry, such as, for example, succinimidoxy or benzotriazoloxy, and n represents 0–10.

Condensing agents are used in the case where X represents hydroxyl. These condensing agents are known, and it is possible to use, for example, carbodiimides such as dicyclohexylcarbodiimide or diisopropylcarbodiimide.

Preferred compounds of the formula (IV) are those in which $R^4$ represents hydroxyl or a $C_1$-$C_3$-alkyl group, and
X represents halogen or $C_1$-$C_3$-alkyloxy.

In the case where $R^4$ in the dicarboxylic acid derivatives of the formula IV is not equal to hydrogen, to prepare the compounds of the general formula (I) the radical $R^4$ is hydrolyzed under basic or acidic, preferably basic, conditions.

Particularly preferred compounds of the formula (IV) are those in which $R^3$ represents methyloxy or ethyloxy, and in which
$R^4$ represents a hydroxyl group.

These particularly preferred compounds of the formula IV react with the amines of the formula II or III with the formation of an amide bond, the reaction taking place being known in organic chemistry as aminolysis of a carboxylic ester.

In variant B, compounds of the general formulae (II) and (III) are reacted with cyclic anhydrides of the formula (V)

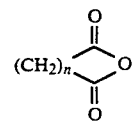

in which n preferably represents 2 or 3, to give the compounds according to the invention, of the general formula (I).

The process variants A and B according to the invention for the preparation of the compounds of the formula (I) can be represented diagrammatically as follows:

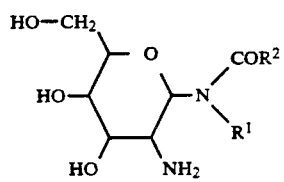

II

+

Variant A or

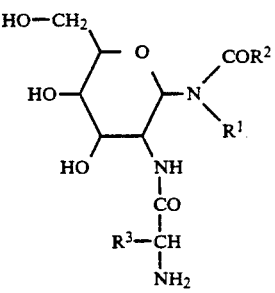

III

+

Variant B

-continued

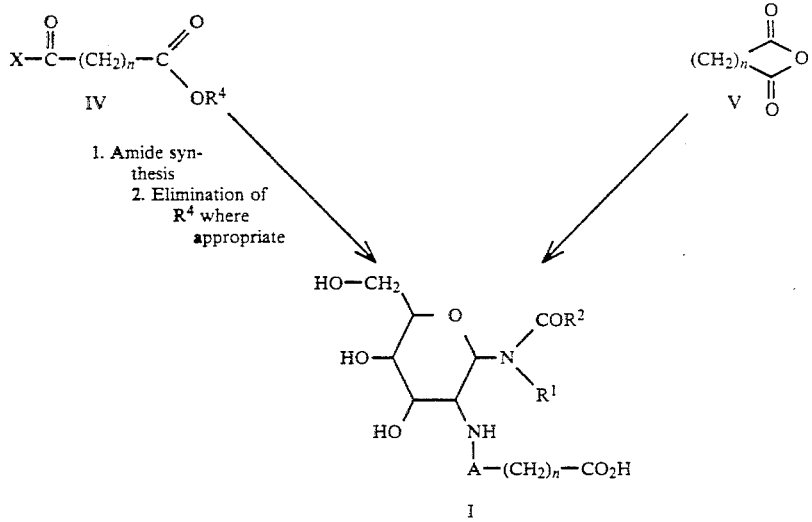

$R^1$, $R^2$, $R^3$ and $R^4$, X and n have the above-mentioned meaning.

A represents either the group —CO— or a radical CO—CH—NH—CO.

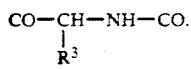

Suitable diluents for the process are polar organic solvents. These include, for example, methanol, THF, DMF and dioxane.

Generally used in the case of process variant A is a reaction temperature of about 50° C., and for process variant B is room temperature.

The ratio of the amounts of the reactants is varied in some of the below described examples. In general, equimolar amounts are used. It has proved expedient in variant A to use the dicarboxylic acid derivatives in a 1 to 1.5-fold molar ratio.

The compounds of the formulae II + III have already been disclosed or can be prepared by known methods (compare EP-A 091,645 and EP-A 206,037).

The present invention also relates to agents which improve the body's intrinsic defenses. It is customary to administer vaccines together with adjuvants, that is to say with substances which enhance the formation of antibodies. Used for these purposes is, for example, Freund's complete adjuvant. This takes the form of a water-in-oil emulsion to which killed Mycobacteria have been added. Apart from the formation of antibodies, the killed Mycobacteria are able to stimulate cell-mediated immunity and macrophage activity.

It has now been found that the compounds according to the invention, of the general formula I whose definitions are stated above, increase the non-specific defenses against infections.

The compounds have broad defense-stimulating actions.

Substances which stimulate the body's intrinsic defences (immune system, phagocytosis) during an infection are of great interest both for human and for veterinary medicine because, without assistance from the body's intrinsic defense mechanisms, many infections persist despite good chemotherapeutic options. This may result in renewed appearance of symptoms (recurrence) after the first appearance of the disease has been overcome, and thus in chronic recurrent illnesses. Among the diseases caused by bacteria, the particular problems are represented by infections with facultative intracellular bacteria. An experimental model for a disease of this type is infection of the mouse with *Salmonella typhimurium*. After the mice have been inoculated with these human-pathogenic bacteria, the course of the illness depends on the infective dose and is subacute to chronic, with the first of the animals dying after 4 to 7 days. During this period there is the possibility of influencing the immune system by substances. High organism counts are found in the blood, in the liver and in the spleen of infected animals during the first two weeks. The organism counts then gradually decrease but are still detectable 8-12 weeks after the inoculation.

The following effects have been found experimentally:

1. Effects on the organism counts in blood and liver

Compound of Example 13 g

The compound 13 g was administered once intraperitoneally in various doses to mice on the day before intraperitoneal infection with $2 \times 10^5$ colony-forming units (CFU) of *Salmonella typhimurium*. In untreated animals, this infective dose results in a high organism count in the blood and in the organs, especially in liver and spleen, on day 3.

In several experiments (see Table 1) there was, after treatment of the animals with 1 mg/kg or 10 mg/kg active compound, a distinct reduction in the organism counts in the blood and in the liver of infected mice compared with animals which had received only the diluent (control). Since the substances show no direct effect on the in vitro multiplication of *Salmonella typhimurium* the results are an indication that the defense mechanisms of the host are enhanced.

TABLE 1

| Effect of the compound of Example 13g on the organism counts in blood and liver | | |
|---|---|---|
| Dose[a] (mg/kg) | [b]CFU/ml of blood | CFU/g of liver |
| Control | $10^{3.5} \pm 1.9$ | $10^{6.9} \pm 1.5$ |
| 1 | $10^{1.7} \pm 0.9$ | $10^{4.7} \pm 2.0$ |

TABLE 1-continued

Effect of the compound of Example 13g on the organism counts in blood and liver

| Dose[a] (mg/kg) | [b]CFU/ml of blood | CFU/g of liver |
|---|---|---|
| 10 | $10^{1.2} \pm 0.6$ | $10^{5.6} \pm 0.5$ |

[a]single i.p. 24 h before infection
[b]CFU: colony-forming units

2. Effect on the survival rate and survival time

Administration of the compounds according to the invention also resulted in an increase in the survival rate and in a more rapid disappearance of the symptoms of illness. Examples:

The compounds of Example 13 g or Example 5 g were administered once subcutaneously to mice before lethal infection with *S. typhimurium* (Tables 2 and 3). In doses of 0.1, 1.0 or 10 mg/kg, the substances brought about an increase in the survival rate and a prolongation of the survival time. Similar effects were also observed after infection with other bacteria. The animals were female outbred mice of the CF1 strain (weight 18-20 g). They were housed in Makrolon cages under constant conditions (22± 2° C.; 55-65% relative humidity) and received Ssniff experimental animal diet.

TABLE 2

Effect of the compound of Example 13g on the survival rate and on the survival time of mice after lethal infection with *Salmonella typhimurium*

| Dose[a] | Survival rate on day 28 after infection | [b]Survival time p | (median) |
|---|---|---|---|
| Control | 1/24 (4%) | | 7.5 days |
| 0.1 | 7/24 (29%) | 0.02 | 13.0 days |
| 1.0 | 9/24 (38%) | 0.005 | 10.0 days |
| 10.0 | 11/24 (46%) | 0.0009 | 14.0 days |

[a]single subcutaneous administration 24 h before infection
[b]compared with controls, Fisher's exact test

TABLE 3

Effect of the compound of Example 5g on the survival rate and on the survival time of mice after lethal infection with *Salmonella typhimurium*

| Dose[a] | Survival rate on day 28 after infection | [b]Survival time p | (median) |
|---|---|---|---|
| Control | 0/24 | | 7.5 days |
| 0.1 | 3/24 (13%) | 0.12 | 7.5 days |
| 1.0 | 6/24 (25%) | 0.01 | 8.0 days |
| 10.0 | 9/24 (38%) | 0.0008 | 17.5 days |

[a]single subcutaneous administration 24 h before infection
[b]compared with controls, Fisher's exact test The compounds of the formula I according to the invention additionally show an invitro action on human granulocytes.

Phagocytes are an important constituent of the nonspecific defenses against infection. As the first cellular "line of defense" of the immune system they repulse invading microorganisms and are thus of crucial importance for the subsequent course of the infective event.

Besides various other microbicidal properties, phagocytes are especially able to produce, via oxidative metabolism, toxic reactive oxygen species ($O_2-$, $H_2O_2$, $-OH$, $^1O_2$) with an antimicrobial action.

Figure 1B:
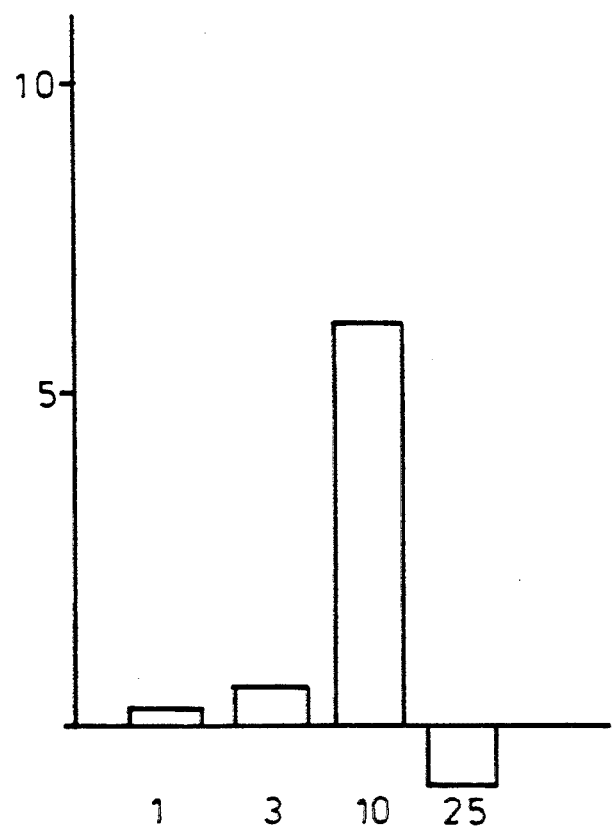

The effect of the compounds according to the invention, of the general formula (I), on oxidative metabolism was tested in appropriate studies. It was shown, here represented by the example of the compound of Example 5 d, that there was a distinct increase in oxidative metabolism measured on the basis of the Listeria-induced chemiluminescence and $O_2$ production of human granulocytes from peripheral blood. In the case of the compound of Example 5 d, a maximum effect was reached at a concentration of 10 $\mu g/10^6$ cells/ml (FIGS. 1a and 1b).

Enhancement of primary humoral immunity against sheep erythrocytes (SE) in vitro It is possible experimentally to induce in vitro the development of a humoral immune response with heterologous red blood cells by primary immunization of mouse spleen cells in suspension cultures (R.I. Mishell and R.W. Dutton, J. Exp. Med. 126, 423 (1967)). For this purpose, Balb/c mouse spleen cells are cultivated for 5 days in the presence of antigen (SE) and the test substance. The cells are harvested, washed and plated out, together with the antigen and complement, in semi-solid agar and incubated at 37° C. for 2 hours (N.K. Jerne, A.A. Nordin and C. Henry, "Cell bound Antibodies", eds. Amos and Koprowski, Wistar Inst. Press, Philadelphia, USA, pp 109 (1963)). The antigen-sensitization of mouse lymphocytes in the primary culture results in the synthesis and release of antibodies. The secreted specific antibodies bind to the SE antigen and lyse these cells owing to the presence of complement (plaque formation). Substances of the present class of compounds are able to increase, dose-dependently in the range 3-100 $\mu g/ml$, the number of antibody-forming cells (Table 4).

TABLE 4

Effects of the compound of Example 13g on antibody synthesis in vitro.
Antibody-secreting cells/culture as a function of the dose $\mu g/ml$

| Dose [$\mu g/ml$] | 0 | 0.1 | 0.3 | 1.0 | 3.0 | 10.0 |
|---|---|---|---|---|---|---|
| Antibody-secreting cells | 1540 | 2100 | 2540 | 7150 | 13800 | 8560 |

The compounds according to the invention can be formulated as pharmaceutical products. Preferred pharmaceutical products are tablets or gelatin capsules which contain the active compound together with the following diluents: for example lactose, dextrose, sucrose, mannitol, sorbitol, cellulose and/or lubricants, for example diatomaceous earth, talc, stearic acid or salts thereof such as magnesium or calcium stearate, and/or polyethylene glycol. Tablets additionally contain binders, for example magnesium aluminum silicate, starches such as maize, wheat, rice or arrowroot starch, gelatin, tragacanth, methylcellulose, sodium carboxymethylcellulose and/or polyvinylpyrrolidone and, if desired, disintegrants, for example starches, agar, alginic acid or a salt thereof, such as sodium alginate, and/or effervescent mixtures, or adsorbents, pigments, flavorings and sweeteners. Injectable products are preferably isotonic aqueous solutions or suspensions. Suppositories, ointments or creams are primarily fatty emulsions or suspensions. The pharmaceutical products of the present invention can be sterilized and/or contain auxiliaries, for example preservatives, stabilizers, wetting agents and/or emulsifiers, solubilizers, salts to regulate the osmotic pressure and/or buffers. The present pharmaceutical products, which, if desired, can contain other pharmacologically valuable substances, are prepared in a manner known per se, for example using conventional mixing, granulating or coating processes, and contain from about 0.1% to about 75%, in particular from about 1% to 50%, of the said active compounds.

The products of the present invention which are also administered can also be provided with a coating resistant to gastric juice.

The new active compounds can be used as defense-enhancing and immunopotentiating agents for the treatment of chronic and acute infections (for example bacterial, viral and parasitic) and malignant tumours. They can additionally be used as adjuvants in vaccination to stimulate phagocytosis and to modulate the defense and immune systems.

The compounds according to the invention and their pharmaceutically utilizable non-toxic salts are distinguished by being readily soluble in polar solvents, preferably in water, with the activity surprisingly being retained.

EXAMPLES

The thin-layer chromatography (TLC) was carried out on precoated silica gel TLC plates (E. Merck, Darmstadt), and the preparative separations were carried out with silica gel 60 (Merck, Darmstadt).

General procedure for the reaction with acyclic dicarboxylic monoalkyl esters (variant A)

1 mmol of the amine component is dissolved in 20 ml of ethanol and, after addition of 1 mmol of dicarboxylic monoalkyl ester and 1 ml of 1 N sodium hydroxide solution, stirred overnight. The reaction mixture is evaporated in vacuo, and the residue is taken up in 5 ml of ethanol and 50 ml of water and freeze-dried.

General procedure for the reaction with cyclic dicarboxylic anhydrides (variant B)

1 mmol of the amine component is dissolved in 20 ml of ethanol and, after addition of 1 mmol of dicarboxylic anhydride, stirred overnight. After reaction is complete, the mixture is neutralized with 1 ml of 1 N sodium hydroxide solution and evaporated in vacuo. The residue is then taken up in 5 ml of ethanol and 50 ml of water and freeze-dried.

EXAMPLE 1

The following compounds are obtained by reacting N-(2-amino-2-deoxy-$\beta$-D-glucopyranosyl)-N-alkylcarboxamides with succinic anhydride (variant B):

1.a  N-[2-(3-carboxypropionylamino)-2-deoxy-$\beta$-D-glucopyranosyl]-N-dodecyl-dodecanamide
1.b  N-[2-(3-carboxypropionylamino)-2-deoxy-$\beta$-D-glucopyranosyl]-N-dodecyl-tetradecanamide
1.c  N-[2-(3-carboxypropionylamino)-2-deoxy-$\beta$-D-glucopyranosyl]-N-dodecyl-octadecanamide
[$\alpha$]$_D$=11.8° (c=0.7 in DMF).
$R_f$=0.13 in CH$_2$Cl$_2$/CH$_3$OH/aqueous NH$_3$=10:3:0.1 (v/v/v).
1.d  N-[2-(3-carboxypropionylamino)-2-deoxy-$\beta$-D-glucopyranosyl]-N-tetradecyl-dodecanamide
1.e  N-[2-(3-Carboxypropionylamino)-2-deoxy-$\beta$-D-glucopyranosyl]-N-tetradecyl-tetradecanamide
1.f  N-[2-(3-Carboxypropionylamino)-2-deoxy-$\beta$-D-glucopyranosyl]-N-tetradecyl-octadecanamide
1.g  N-[2-(3-Carboxypropionylamino)-2-deoxy-$\beta$-D-glucopyranosyl]-N-octadecyl-dodecanamide
[$\alpha$]$_D$=12.0° (c=0.5 in DMF).
$R_f$=0.15 in CH$_2$Cl$_2$/CH$_3$OH/aqueous NH$_3$=10:3:0.1 (v/v/v).
1.h  N-[2-(3-Carboxypropionylamino)-2-deoxy-$\beta$-D-glucopyranosyl]-N-octadecyl-tetradecanamide
1.i  N-[2-(3-carboxypropionylamino)-2-deoxy-$\beta$-D-glucopyranosyl]-N-octadecyl-octadecanamide

EXAMPLE 2

Reaction of N-(2-amino-2-deoxy-$\beta$-D-glucopyranosyl)-N-alkylcarboxamides with glutaric anhydride (variant B)

2.a  N-[2-(4-carboxybutyrylamino)-2-deoxy-$\beta$-D-glucopyranosyl]-N-dodecyl-octadecanamide
[$\alpha$]$_D$=11.6° (c=0.7 in DMF).
2.b  N-[2-(4-carboxybutyrylamino)-2-deoxy-$\beta$-D-glucopyranosyl]-N-tetradecyl-octadecanamide
2.c  N-[2-(4-carboxybutyrylamino)-2-deoxy-$\beta$-D-glucopyranosyl]-N-odctadecyl-dodecanamide
2.d  N-[2-(4-carboxybutyrylamino)-2-deoxy-$\beta$-D-glucopyranosyl]-N-octadecyl-octadecanamide

EXAMPLE 3

Reaction of N-(2-amino-2-deoxy-$\beta$-D-glucopyranosyl)-N-alkylcarboxamides with monomethyl adipate (variant A)

3.a  N-[2-(5-carboxyvalerylamino)-2-deoxy-$\beta$-D-glucopyranosyl]-N-dodecyl-octadecanamide
3.b  N-[2-(5-carboxyvalerylamino)-2-deoxy-$\beta$-D-glucopyranosyl]-N-tetradecyl-octadecanamide
3.c  N-[2-(5-carboxyvalerylamino)-2-deoxy-$\beta$-D-glucopyranosyl]-N-octadecyl-dodecanamide
3.d  N-[2-(5-carboxyvalerylamino)-2-deoxy-$\beta$-D-glucopyranosyl]-N-octadecyl-octadecanamide

EXAMPLE 4

Reaction of N-(2-amino-2-deoxy-$\beta$-D-glucopyranosyl)-N-alkylcarboxamides with monomethyl octanedicarboxylate (variant A)

4.a  N-[2-(7-carboxyheptanoylamino)-2-deoxy-$\beta$-D-glucopyranosyl]-N-dodecyl-octadecanamide
[$\alpha$]$_D$=10.8° (c=0.5 in DMF).
4.b  N-[2-(7-carboxyheptanoylamino)-2-deoxy-$\beta$-D-glucopyranosyl]-N-tetradecyl-octadecanamide
4.c  N-[2-(7-carboxyheptanoylamino)-2-deoxy-$\beta$-D-glucopyranosyl]-N-octadecyl-dodecanamide
4.d  N-[2-(7-carboxyheptanoylamino)-2-deoxy-$\beta$-D-glucopyranosyl]-N-octadecyl-octadecanamide

EXAMPLE 5

Reaction of N-(2-glycylamino-2-deoxy-$\beta$-D-glucopyranosyl)-N-alkylcarboxamides with succinic anhydride (variant B)

5.a  N-{2-[N-(3-carboxypropionyl)-glycyl]-amino-2-deoxy-$\beta$-D-glucopyranosyl}-N-dodecyl-dodecanamide
5.b  N-{2-[N-(3-carboxypropionyl)-glycyl]-amino-2-deoxy-$\beta$-D-glucopyranosyl}-N-dodecyl-tetradecanamide
5.c  N-{2-[N-(3-carboxypropionyl)-glycyl]-amino-2-deoxy-$\beta$-D-glucopyranosyl}-N-dodecyl-octadecanamide
5.d  N-{2-[N-(3-carboxypropionyl)-glycyl]-amino-2-deoxy-$\beta$-D-glucopyranosyl}-N-tetradecyl-dodecanamide
[$\alpha$]$_D$=4.9° (c=1.4 in methanol).
$R_f$=0.15 in CH$_2$Cl$_2$/CH$_3$OH/aqueous NH$_3$=10:3:0.1 (v/v/v).

5.e  N-{2-[N-(3-carboxypropionyl)-glycyl]-amino-2-deoxy-β-D-glucopyranosyl}-N-tetradecyl-tetradecanamide 5.f  N-{2-[N-(3-carboxypropionyl)-glycyl]-amino-2-deoxy-β-D-glucopyranosyl}-N-tetradecyl-octadecanamide 5.g  N-{2-[N-(3-carboxypropionyl)-glycyl]-amino-2-deoxy-β-D-glucopyranosyl}-N-octadecyl-dodecanamide

[α]$_D$ = 8.8° (c=0.5 in DMF).

$R_f$ = 0.10 in $CH_2Cl_2/CH_3OH$/aqueous $NH_3$ = 10:3:0.1 (v/v/v).

5.h  N-{2-[N-(3-carboxypropionyl)-glycyl]-amino-2-deoxy-β-D-glucopyranosyl}-N-octadecyl-tetradecanamide 5.i  N-{2-[N-(3-carboxypropionyl)-glycyl]-amino-2-deoxy-β-D-glucopyranosyl}-N-octadecyl-octadecanamide

EXAMPLE 6

Reaction of N-(2-glycylamino-2-deoxy-β-D-glucopyranosyl)-N-alkylcarboxamides with glutaric anhydride (variant B)

6.a  N-{2-[N-(4-carboxybutyryl)-glycyl]-amino-2-deoxy-62 -D-glucopyranosyl} -N-dodecyl-octadecanamide 6.b  N-{2-[N-(4-carboxybutyryl)-glycyl]-amino-2-deoxy-β-D-glucopyranosyl}-N-tetradecyl-octadecanamide 6.c  N-{2-[N-(4-carboxybutyryl)-glycyl]-amino-2-deoxy-β-D-glucopyranosyl}-N-octadecyl-dodecanamide 6.d  N-{2-[N-(4-carboxybutyryl)-glycyl]-amino-2-deoxy-β-D-glucopyranosyl}-N-octadecyl-octadecanamide

EXAMPLE 7

Reaction of N-(2-glycylamino-2-deoxy-β-D-glucopyranosyl)-N-alkylcarboxamides with monomethyl adipate (variant A)

7.a N-{2-[N-(5-carboxyvaleryl)-glycyl]-amino-2-deoxy-β-D-glucopyranosyl}-N-dodecyl-octadecanamide 7.b N-{2-[N-(5-carboxyvaleryl)-glycyl]-amino-2-deoxy-β-D-glucopyranosyl}-N-tetradecyl-octadecanamide 7.c N-{2-[N-(5-carboxyvaleryl)-glycyl]-amino-2-deoxy-β-D-glucopyranosyl}-N-octadecyl-dodecanamide 7.d N-{2-[N-(5-carboxyvaleryl)-glycyl]-amino-2-deoxy-β-D-glucopyranosyl}-N-octadecyl-octadecanamide

EXAMPLE 8

Reaction of N-(2-glycylamino-2-deoxy-β-D-glucopyranosyl)-N-alkylcarboxamides with monomethyl octanedicarboxylate (variant A)

8.a  N-{2-[N-(7-carboxyheptanoyl)-glycyl]-amino-2-deoxy-β-D-glucopyranosyl}-N-dodecyl-octadecanamide 8.b  N-{2-[N-(7-carboxyheptanoyl)-glycyl]-amino-2-deoxy-β-D-glucopyranosyl}-N-tetradecyl-octadecanamide 8.c  N-{2-[N-(7-carboxyheptanoyl)-glycyl]-amino-2-deoxy-β-D-glucopyranosyl}-N-octadecyl-dodecanamide 8.d  N-{2-[N-(7-carboxyheptanoyl)-glycyl]-amino-2-deoxy-β-D-glucopyranosyl}-N-octadecyl-octadecanamide

EXAMPLE 9

Reaction of N-(2-L-alanylamino-2-deoxy-β-D-glucopyranosyl)-N-alkylcarboxamides with succinic anhydride (variant B)

9.a  N-{2-[N-(3-carboxypropionyl)-L-alanyl]-amino-2-deoxy-β-D-glucopyranosyl} -N-dodecyl-octadecanamide 9.b  N-{2-[N-(3-carboxypropionyl)-L-alanyl]-amino-2-deoxy-β-D-glucopyranosyl}-N-tetradecyl-octadecanamide 9.c  N-{2-[N-(3-carboxypropionyl)-L-alanyl]-amino-2-deoxy-β-D-glucopyranosyl}-N-octadecyl-dodecanamide 9.d  N-{2-[N-(3-carboxypropionyl)-L-alanyl]-amino-2-deoxy-β-D-glucopyranosyl}-N-octadecyl-octadecanamide

EXAMPLE 10

Reaction of N-(2-L-alanylamino-2-deoxy-β-D-glucopyranosyl)-N-alkylcarboxamides with glutaric anhydride (variant B)

10.a  N-{2-[N-(4-carboxybutyryl)-L-alanyl]-amino-2-deoxy-β-D-glucopyranosyl}-N-dodecyl-octadecanamide 10.b  N-{2-[N-(4-carboxybutyryl)-L-alanyl]-amino-2-deoxy-β-D-glucopyranosyl}-N-tetradecyl-octadecanamid 10.c  N-{2-[N-(4-carboxybutyryl)-L-alanyl]-amino-2-deoxy-β-D-glucopyranosyl}-N-octadecyl-dodecanamide 10.d  N-{2-[N-(4-carboxybutyryl)-L-alanyl]-amino-2-deoxy-β-D-glucopyranosyl}-N-octadecyl-octadecanamide

EXAMPLE 11

Reaction of N-(2-L-alanylamino-2-deoxy-β-D-glucopyranosyl)-N-alkylcarboxamides with monomethyl adipate (variant A).

11.a  N-{2-[N-(5-carboxyvaleryl)-L-alanyl]-amino-2-deoxy-β-D-glucopyranosyl}-N-dodecyl-octadecanamide 11.b  N-{2-[N-(5-carboxyvaleryl)-L-alanyl]-amino-2-deoxy-β-D-glucopyranosyl}-N-tetradecyl-octadecanamide 11.c  N-{2-[N-(5-carboxyvaleryl)-L-alanyl]-amino-2-deoxy-β-D-glucopyranosyl}-N-octadecyl-dodecanamide 11.d  N-{2-[N-(5-carboxyvaleryl)-L-alanyl]-amino-2-deoxy-β-D-glucopyranosyl}-N-octadecyl-octadecanamide

EXAMPLE 12

Reaction of N-(2-L-alanylamino-2-deoxy-β-D-glucopyranosyl)-N-alkyl-carboxamides with monomethyl octanedicarboxylate (variant A)

12.a N-{2-[N-(8-carboxyheptanoyl)-L-alanyl]-amino-2-deoxy-β-D-glucopyranosyl} -N-dodecyl-octadecanamide 12.b N-{2-[N-(8-carboxyheptanoyl)-L-alanyl]-amino-2-deoxy-β-D-glucopyranosyl}-N-tetradecyl-octadecanamide 12.c N-{2-[N-(8-carboxyheptanoyl)-L-alanyl]-amino-2-deoxy-β-D-glucopyranosyl}-N-octadecyl-dodecanamide 12.d N-{2-[N-(8-carboxyheptanoyl)-L-alanyl]-amino-2-deoxy-β-D-glucopyranosyl}-N-octadecyl-octadecanamide

EXAMPLE 13

Reaction of N-(2-L-leucylamino-2-deoxy-β-D-glucopyranosyl)-N-alkylcarboxamides with succinic anhydride (variant B)

13.a N-{2-[N-(3-carboxypropionyl)-L-leucyl]-amino-2-deoxy-β-D-glucopyranosyl}-N-dodecyl-dodecanamide 13.b N-{2-[N-(3-carboxypropionyl)-L-leucyl]-amino-2-deoxy-β-D-glucopyranosyl}-N-dodecyl-tetradecanamide 13.c N-{2-[N-(3-carboxypropionyl)-L-leucyl]-amino-2-deoxy-β-D-glucopyranosyl}-N-dodecyl-octadecanamide $R_f = 0.13$ in $CH_2Cl_2/CH_3OH$/aqueous $NH_3 = 10:3:0.1$ (v/v/v).

13.d N-{2-[N-(3-carboxypropionyl)-L-leucyl]-amino-2-deoxy-β-D-glucopyranosyl}-N-tetradecyl-dodecanamide 13.e N-{2-[N-(3-carboxypropionyl)-L-leucyl]-amino-2-deoxy-β-D-glucopyranosyl}-N-tetradecyl-tetradecanamide 13.f N-{2-[N-(3-carboxypropionyl)-L-leucyl]-amino-2-deoxy-β-D-glucopyranosyl}-N-tetradecyl-octadecanamide 13.g N-{2-[N-(3-carboxypropionyl)-L-leucyl]-amino-2-deoxy-β-D-glucopyranosyl}-N-octadecyl-dodecanamide $R_f = 0.15$ in $CH_2Cl_2/CH_3OH$/aqueous $NH_3 = 10:3:0.1$ (v/v/v).

13.h N-{2-[(3-carboxypropionyl)-L-leucyl]-amino-2-deoxy-β-D-glucopyranosyl}-N-octadecyl-tetradecanamide 13.i N-{2-[N-(3-carboxypropionyl)-L-leucyl]-amino-2-deoxy-β-D-glucopyranosyl}-N-octadecyl-octadecanamide

EXAMPLE 14

Reaction of N-(2-L-leucylamino-2-deoxy-β-D-glucopyranosyl)-N-alkylcarboxamides with glutaric anhydride (variant B)

14.a N-{2-[N-(4-carboxybutyryl)-L-leucyl]-amino-2-deoxy-β-D-glucopyranosyl}-N-dodecyl-octadecanamide 14.b N-{2-[N-(4-carboxybutyryl)-L-leucyl]-amino-2-deoxy-β-D-glucopyranosyl}-N-tetradecyl-octadecanamide 14.c N-{2-[N-(4-carboxybutyryl)-L-leucyl]-amino-2-deoxy-β-D-glucopyranosyl}-N-octadecyl-dodecanamide 14.d N-{2-[N-(4-carboxybutyryl)-L-leucyl]-amino-2-deoxy-β-D-glucopyranosyl}-N-octadecyl-octadecanamide

EXAMPLE 15

Reaction of N-(2-L-leucylamino-2-deoxy-β-D-glucopyranosyl)-N-alkylcarboxamides with monomethyl adipate (variant A)

15.a N-{2-[N-(5-carboxyvaleryl)-L-leucyl]-amino-2-deoxy-β-D-glucopyranosyl}-N-dodecyl-octadecanamide 15.b N-{2-[N-(5-carboxyvaleryl)-L-leucyl]-amino-2-deoxy-β-D-glucopyranosyl}-N-tetradecyl-octadecanamide 15.c N-{2-[N-(5-carboxyvaleryl)-L-leucyl]-amino-2-deoxy-β-D-glucopyranosyl}-N-octadecyl-dodecanamide 15.d N-{2-[N-(5-carboxyvaleryl)-L-leucyl]amino-2-deoxy-β-D-glucopyranosyl}-N-octadecyl-octadecanamide

EXAMPLE 16

Reaction of N-(2-L-leucylamino-2-deoxy-β-D-glucopyranosyl)-N-alkylcarboxamides with monomethyl octanedicarboxylate (variant A)

16.a N-{2-[N-(7-carboxyheptanoyl)-L-leucyl]-amino-2-deoxy-β-D-glucopyranosyl}-N-dodecyl-octadecanamide 16.b N-{2-[N-(7-carboxyheptanoyl)-L-leucyl]-amino-2-deoxy-β-D-glucopyranosyl}-N-tetradecyl-octadecanamide 16.c N-{2-[N-(7-carboxyheptanoyl)-L-leucyl]-amino-2-deoxy-β-D-glucopyranosyl}-N-octadecyl-dodecanamide 16.d N-{2-[N-(7-carboxyheptanoyl)-L-leucyl]-amino-2-deoxy-β-D-glucopyranosyl}-N-octadecyl-octadecanamide

EXAMPLE 17

Reaction of N-(2-L-serylamino-2-deoxy-β-D-glucopyranosyl)-N-alkylcarboxamides with succinic anhydride (variant B)

17.a N-{2-[N-(3-carboxypropionyl)-L-seryl]-amino-2-deoxy-β-D-glucopyranosyl}-N-dodecyl-octadecanamide 17.b N-{2-[N-(3-carboxypropionyl)-L-seryl]-amino-2-deoxy-β-D-glucopyranosyl}-N-tetradecyl-octadecanamide 17.c N-{2-[N-(carboxypropionyl)-L-seryl]-amino-2-deoxy-β-D-glucopyranosyl}-N-octadecyl-dodecanamide 17.d N-{2-[N-(3-carboxypropionyl)-L-seryl]-amino-2-deoxy-β-D-glucopyranosyl}-N-octadecyl-octadecanamide

EXAMPLE 18

Reaction of N-(2-L-serylamino-2-deoxy-β-D-glucopyranosyl)-N-alkylcarboxamides with glutaric anhydride (variant B)

18.a N-{2-[N-(4-carboxybutyryl)-L-seryl]-amino-2-deoxy-β-D-glucopyranosyl}-N-dodecyl-octadecanamide 18.b N-{2-[N-(4-carboxybutyryl)-L-seryl]-amino-2-deoxy-β-D-glucopyranosyl}-N-tetradecyl-octadecanamide 18.c N-{2-[N-(4-carboxybutyryl)-L-seryl]-amino-2-deoxy-β-D-glucopyranosyl}-N-octadecyl-dodecanamide 18.d N-{2-[N-(4-carboxybutyryl)-L-seryl]-amino-2-deoxy-β-D-glucopyranosyl}-N-octadecyl-octadecanamide

EXAMPLE 19

Reaction of N-(2-L-serylamino-2-deoxy-β-D-glucopyranosyl)-N-alkylcarboxamides with monomethyl adipate (variant A)

19.a N-{2-[N-(5-carboxyvaleryl)-L-seryl]-amino-2-deoxy-β-D-glucopyranosyl}-N-dodecyl-octadecanamide 19.b N-{2-[N-(5-carboxyvaleryl)-L-seryl]-amino-2-deoxy-β-D-glucopyranosyl}-N-tetradecyl-octadecanamide 19.c N-{2-[N-(5-carboxyvaleryl)-L-seryl]-amino-2-deoxy-β-D-glucopyranosyl}-N-octadecyl-dodecanamide 19.d  N-{2-[N-(5-carboxyvaleryl)-L-seryl]-amino-2-deoxy-β-D-glucopyranosyl}-N-octadecyl-octadecanamide

EXAMPLE 20

Reaction of N-(2-L-serylamino-2-deoxy-β-D-glucopyranosyl)-N-alkylcarboxamides with monomethyl octanedicarboxylate (variant A)
20.a  N-{2-[N-(7-carboxyheptanoyl)-L-seryl]-amino-2-deoxy-β-D-glucopyranosyl}-N-dodecyl-octadecanamide
20.b  N-{2-[N-(7-carboxyheptanoyl)-L-seryl]-amino-2-deoxy-β-D-glucopyranosyl}-N-tetradecyl-octadecamide
20.c  N-{2-[N-(7-carboxyheptanoyl)-L-seryl]-amino-2-deoxy-β-D-glucopyranosyl}-N-octadecyl-dodecanamide
20.d  N-{2-[N-(7-carboxyheptanoyl)-L-seryl]-amino-2-deoxy-β-D-glucopyranosyl}-N-octadecyl-octadecanamid

EXAMPLE 21

Reaction of N-(2-L-phenylalanylamino-2-deoxy-β-D-glucopyranosyl)-N-alkylcarboxamides with succinic anhydride (variant B)
21.a  N-{2-[N-(3-carboxypropionyl)-L-phenylalanyl]-amino-2-deoxy-β-D-glucopyranosyl}-N-dodecyl-octadecanamide
21.b  N-{2-[N-(3-carboxypropionyl)-L-phenylalanyl]-amino-2-deoxy-β-D-glucopyranosyl}-N-tetradecyl-octadecanamide
21.c  N-{2-[N-(3-carboxypropionyl)-L-phenylalanyl]-amino-2-deoxy-β-D-glucopyranosyl}-N-octadecyl-dodecanamide
21.d  N-{2-[N-(3-carboxypropionyl)-L-phenylalanyl]-amino-2-deoxy-β-D-glucopyranosyl}-N-octadecyl-octadecanamide

EXAMPLE 22

Reaction of N-(2-L-phenylalanylamino-2-deoxy-β-D-glucopyranosyl)-N-alkylcarboxamides with glutaric anhydride (variant B)
22.a  N-{2-[N-(4-carboxybutyryl)-L-phenylalanyl]-amino-2-β-D-glucopyranosyl}-N-dodecyl-octadecanamide
22.b  N-{2-[N-(4-carboxybutyryl)-L-phenylalanyl]-amino-2-β-D-glucopyranosyl}-N-tetradecyl-octadecanamide
22.c  N-{2-[N-(4-carboxybutyryl)-L-phenylalanyl]-amino-2-β-D-glucopyranosyl}-N-octyl-dodecanamide
22.d  N-{2-[N-(4-carboxybutyryl)-L-phenylalanyl]-amino-2-β-D-glucopyranosyl}-N-octadecyl-octadecanamide

EXAMPLE 23

Reaction of N-(2-L-phenylalanylamino-2-deoxy-β-D-glucopyranosyl)-N-alkylcarboxamides with monomethyl adipate (variant A)
23.a  N-{2-[N-(5-carboxyvaleryl)-L-phenylalanyl]-amino-2-deoxy-β-D-glucopyranosyl}-N-dodecyl-octadecanamide
23.b  N-{2-[N-(5-carboxyvaleryl)-L-phenylalanyl]-amino-2-deoxy-β-D-glucopyranosyl}-N-tetradecyl-octadecanamide
23.c  N-{2-[N-(5-carboxyvaleryl)-L-phenylalanyl]-amino-2-deoxy-β-D-glucopyranosyl}-N-octadecyl-dodecanamide
23.d  N-{2-[N-(5-carboxyvaleryl)-L-phenylalanyl]-amino-2-deoxy-β-D-glucopyranosyl}-N-octadecyl-octadecanamide

EXAMPLE 24

Reaction of N-(2-L-phenylalanylamino-2-deoxy-β-D-glucopyranosyl)-N-alkylcarboxamides with monomethyl octanedicarboxylate (variant A)
24.a  N-{2-[N-(7-carboxyheptanoyl)-L-phenylalanyl]-amino-2-deoxy-β-D-glucopyranosyl}-N-dodecyl-octadecanamide
24.b  N-{2-[N-(7-carboxyheptanoyl)-L-phenylalanyl]-amino-2-deoxy-β-D-glucopyranosyl}-N-tetradecyl-octadecanamide
24.c  N-{2-[N-(7-carboxyheptanoyl)-L-phenylalanyl]-amino-2-deoxy-β-D-glucopyranosyl}-N-octadecyl-dodecanamide
24.d  N-{2-[N-(7-carboxyheptanoyl)-L-phenylalanyl]-amino-2-deoxy-β-D-glucopyranosyl}-N-octadecyl-octadecanamide

EXAMPLE 25

Reaction of N-(2-amino-2-deoxy-β-D-galactopyranosyl)-N-alkylcarboxamides with succinic anhydride (variant B)
25.a  N-[2-(3-carboxypropionylamino)-2-deoxy-β-D-galactopyranosyl]-N-dodecyl-dodecanamide
25.b  N-[2-(3-carboxypropionylamino)-2-deoxy-β-D-galactopyranosyl]-N-dodecyl-tetradecanamide
25.c  N-[2-(3-carboxypropionylamino)-2-deoxy-β-D-galactopyranosyl]-N-dodecyl-octadecanamide
25.d  N-[2-(3-carboxypropionylamino)-2-deoxy-β-D-galactopyranosyl]-N-tetradecyl-dodecanamide
25.e  N-[2-(3-carboxypropionylamino)-2-deoxy-β-D-galactopyranosyl]-N-tetradecyl-tetradecanamide
25.f  N-[2-(3-carboxypropionylamino)-2-deoxy-β-D-galactopyranosyl]-N-tetradecyl-octadecanamide
25.g  N-[2-(3-carboxypropionylamino)-2-deoxy-β-D-galactopyranosyl]-N-octadecyl-dodecanamide
25.h  N-[2-(3-carboxypropionylamino)-2-deoxy-β-D-galactopyranosyl]-N-octadecyl-tetradecanamide
25.i  N-[2-(3-carboxypropionylamino)-2-deoxy-β-D-galactopyranosyl]-N-octadecyl-octadecanamide

EXAMPLE 26

Reaction of N-(2-amino-2-deoxy-β-D-galactopyranosyl)-N-alkylcarboxamides with glutaric anhydride (variant B)
26.a  N-[2-(4-carboxybutyrylamino)-2-deoxy-β-D-galactopyranosyl]-N-dodecyl-octadecanamide
26.b  N-[2-(4-carboxybutyrylamino)-2-deoxy-β-D-galactopyranosyl]-N-tetradecyl-octadecanamide
26.c  N-[2-(4-carboxybutyrylamino)-2-deoxy-β-D-galactopyranosyl]-N-octadecyl-dodecanamide
26.d  N-[2-(4-carboxybutyrylamino)-2-deoxy-β-D-galactopyranosyl]-N-octadecyl-octadecanamide

EXAMPLE 27

Reaction of N-(2-amino-2-deoxy-β-D-galactopyranosyl)-N-alkylcarboxamides with monomethyl adipate (variant A)
27.a  N-[2-5-carboxyvalerylamino)-2-deoxy-β-D-galactopyranosyl]-N-dodecyl-octadecanamide
27.b  N-[2-5-carboxyvalerylamino)-2-deoxy-β-D-galactopyranosyl]-N-tetradecyl-octadecanamide
27.c  N-[2-5-carboxyvalerylamino)-2-deoxy-β-D-galactopyranosyl]-N-octadecyl-dodecanamide 27.d N-[2-5-carboxyvalerylamino)-2-deoxy-β-D-galactopyranosyl]-N-octadecyl-octadecanamide

EXAMPLE 28

Reaction of N-(2-amino-2-deoxy-β-D-galactopyranosyl)-N-alkylcarboxamides with monomethyl octanedicarboxylate (variant A)

28.a N-[2-(7-carboxyheptanoylamino)-2-deoxy-β-D-galactopyranosyl]-N-dodecyl-octadecanamide 28.b N-[2-(7-carboxyheptanoylamino)-2-deoxy-β-D-galactopyranosyl]-N-tetradecyl-octadecanamide 28.c N-[2-(7-carboxyheptanoylamino)-2-deoxy-β-D-galactopyranosyl]-N-octadecyl-dodecanamide 28.d N-[2-(7-carboxyheptanoylamino)-2-deoxy-β-D-galactopyranosyl]-N-octadecyl-octadecanamide

EXAMPLE 29

Reaction of N-(2-glycylamino-2-deoxy-β-D-galactopyranosyl)-N-alkylcarboxamides with succinic anhydride (variant B)

29.a N-{2-[N-(3-carboxypropionyl)-glycyl]-amino-2-deoxy-β-D-galactopyranosyl}-N-dodecyl-dodecanamide 29.b N-{2-[N-(3-carboxypropionyl)-glycyl]-amino-2-deoxy-β-D-galactopyranosyl}-N-dodecyl-tetradecanamide 29.c N-{2-[N-(3-carboxypropionyl)-glycyl]-amino-2-deoxy-β-D-galactopyranosyl}-N-dodecyl-octadecanamide 29.d N-{2-[N-(3-carboxypropionyl)-glycyl]-amino-2-deoxy-β-D-galactopyranosyl}-N-tetradecyl-dodecanamide 29.e N-{2-[N-(3-carboxypropionyl)-glycyl]-amino-2-deoxy-β-D-galactopyranosyl}-N-tetradecyl-tetradecanamide 29.f N-{2-[N-(3-carboxypropionyl)-glycyl]-amino-2-deoxy-β-D-galactopyranosyl}-N-tetradecyl-octadecanamide 29.g N-{2-[N-(3-carboxypropionyl)-glycyl]-amino-2-deoxy-β-D-galactopyranosyl}-N-octadecyl-dodecanamide 29.h N-{2-[N-(3-carboxypropionyl)-glycyl]-amino-2-deoxy-β-D-galactopyranosyl}-N-octadecyl-tetradecanamide 29.i N-{2-[N-(3-carboxypropionyl)-glycyl]-amino-2-deoxy-β-D-galactopyranosyl}-N-octadecyl-octadecanamide

What is claimed is:

1. A compound of the formula

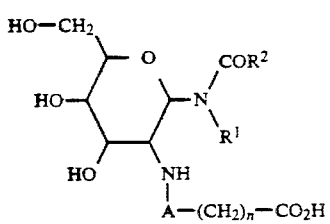

in which $R^1$ denotes an alkyl radical or alkenyl radical having up to 50 carbon atoms, $R^2$ denotes an alkyl radical or an alkenyl radical having up to 50 carbon atoms, A represents —CO— or represents a group

in which $R^3$ represents hydrogen, $C_1$-$C_7$ alkyl, hydroxymethyl, 1-hydroxyethyl, mercaptomethyl, 2-methyl-thioethyl, 3-aminopropyl, 3-ureidopropyl, 3-guanidylpropyl, 4-aminobutyl, carboxymethyl, carbamoyl-methyl, 2-carboxyethyl, 2-carbamoylethyl, benzyl, 4-hydroxybenzyl, 3-indolylmethyl or 4-imidazolyl-methyl, and n represents 0 to 10 and pharmaceutically acceptable salts thereof.

2. A compound according to claim 1, in which $R^1$ and $R^2$ represents alkyl or alkenyl radicals having up to 30 carbon atoms.

3. A compound according to claim 2, in which $R^1$ and $R^2$ represent alkyl or alkenyl radicals having 10 to 20 carbon atoms.

4. A compound according to claim 1, in which
A represents the group

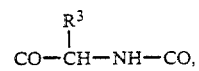

in which $R^3$ represents hydrogen, $C_1$-$C_7$-alkyl, hydroxymethyl, 1-hydroxyethyl, carboxymethyl, 2-carboxyethyl, benzyl or 4-hydroxybenzyl.

5. A compound according to claim 1, in which
A represents the D or L isomers of the amino acids: glycine, sarosine, hippuric acid, alanine, valine, leucine, isoleucine, serine, threonine, cysteine, methionine, ornithine, citrulline, arginine, aspartic acid, asparagine, glutamic acid, glutamine, phenylalanine, tyrosine, proline, tryptophan or histidine, or represents the amino carboxylic acids: α-aminobutyric acid or α-aminoheptanoic acid.

6. A compound according to claim 1 selected from the group consisting of:
N-[2-(3-carboxypropionylamino)-2-deoxy-β-D-glucopyranosyl]-N-dodecyl-dodecanamide,
N-[2-(3-carboxypropionylamino)-2-deoxy-β-D-glucopyranosyl]-N-dodecyl-tetradecanamide,
N-[2-(3-carboxypropionylamino)-2-deoxy-β-D-glucopyranosyl]-N-dodecyl-octadecanamide,
N-[2-(3-carboxypropionylamino)-2-deoxy-β-D-glucopyranosyl]-N-tetradecyl-dodecanamide,
N-[2-(3-Carboxypropionylamino)-2-deoxy-β-D-glucopyranosyl]-N-tetradecyl-tetradecanamide,
N-[2-(3-Carboxypropionylamino)-2-deoxy-β-D-glucopyranosyl]-N-tetradecyl-octadecanamide,
N-[2-(3-Carboxypropionylamino)-2-deoxy-β-D-glucopyranosyl]-N-octadecyl-dodecanamide,
N-[2-(3-Carboxypropionylamino)-2-deoxy-β-D-glucopyranosyl]-N-octadecyl-tetradecanamide,
N-[2-(3-carboxypropionylamino)-2-deoxy-β-D-glucopyranosyl]-N-octadecyl-octadecanamide,
N-[2-(4-carboxybutyrylamino)-2-deoxy-β-D-glucopyranosyl]-N-tetradecyl-octadecanamide,
N-[2-(4-carboxybutyrylamino)-2-deoxy-β-D-glucopyranosyl]-N-tetradecyl-octadecanamide,
N-[2-(4-carboxybutyrylamino)-2-deoxy-β-D-glucopyranosyl]-N-odctadecyl-dodecanamide, N-[2-(4-carboxybutyrylamino)-2-deoxy-β-D-glucopyranosyl]-N-octadecyl-octadecanamide,
N-[2-(5-carboxyvalerylamino)-2-deoxy-β-D-glucopyranosyl]-N-dodecyl-octadecanamide,
N-[2-(5-carboxyvalerylamino)-2-deoxy-β-D-glucopyranosyl]-N-tetradecyl-octadecanamide,
N-[2-(5-carboxyvalerylamino)-2-deoxy-β-D-glucopyranosyl]-N-octadecyl-dodecanamide,
N-[2-(5-carboxyvalerylamino)-2-deoxy-β-D-glucopyranosyl]-N-octadecyl-octadecanamide,
N-[2-(7-carboxyheptanoylamino)-2-deoxy-β-D-glucopyranosyl]-N-dodecyl-octadecanamide,
N-[2-(7-carboxyheptanoylamino)-2-deoxy-β-D-glucopyranosyl] -N-tetradecyl-octadecanamide,
N-[2-(7-carboxyheptanoylamino)-2-deoxy-β-D-glucopyranosyl]-N-octadecyl-dodecanamide,
N-[2-(7-carboxyheptanoylamino)-2-deoxy-β-D-glucopyranosyl]-N-octadecyl-octadecanamide,
N-{2-[N-(3-carboxypropionyl)-glycyl]-amino-2-deoxy-β-D-glucopyranosyl}-N-dodecyl-dodecanamide,
N-{2-[N-(3-carboxypropionyl)-glycyl]-amino-2-deoxy-β-D-glucopyranosyl}-N-dodecyl-tetradecanamide,
N-{2-[N-(3-carboxypropionyl)-glycyl]-amino-2-deoxy-β-D-glucopyranosyl}-N-dodecyl-octadecanamide,
N-{2-[N-(3-carboxypropionyl)-glycyl]-amino-2-deoxy-β-D-glucopyranosyl}-N-tetradecyl-dodecanamide,
N-{2-[N-(3-carboxypropionyl)-glycyl]-amino-2-deoxy-β-D-glucopyranosyl}-N-tetradecyl-tetradecanamide,
N-{2-[N-(3-carboxypropionyl)-glycyl]-amino-2-deoxy-β-D-glucopyranosyl}-N-tetradecyl-octadecanamide,
N-{2-[N-(3-carboxypropionyl)-glycyl]-amino-2-deoxy-β-D-glucopyranosyl}-N-octadecyl-dodecanamide,
N-{2-[N-(3-carboxypropionyl)-glycyl]-amino-2-deoxy-β-D-glucopyranosyl}-N-octadecyl-tetradecanamide,
N-{2-[N-(3-carboxypropionyl)-glycyl]-amino-2-deoxy-β-D-glucopyranosyl}-N-octadecyl-octadecanamide,
N-{2-[N-(4-carboxybutyryl)-glycyl]-amino-2-deoxy-β-D-glucopyranosyl}-N-dodecyl-octadecanamide,
N-{2-[N-(4-carboxybutyryl)-glycyl]-amino-2-deoxy-β-D-glucopyranosyl}-N-tetradecyl-octadecanamide,
N-{2-[N-(4-carboxybutyryl)-glycyl]-amino-2-deoxy-β-D-glycopyranosyl}-N-octadecyl-dodecanamide,
N-{2-[N-(4-carboxybutyryl)-glycyl]-amino-2-deoxy-β-D-glucopyranosyl}-N-octadecyl-octadecanamide,
N-{2-[N-(5-carboxyvaleryl)-glycyl]-amino-2-deoxy-β-D-glucopyranosyl}-N-dodecyl-octadecanamide,
N-{2-[N-(5-carboxyvaleryl)-glycyl]-amino-2-deoxy-β-D-glucopyranosyl}-N-tetradecyl-octadecanamide,
N-{2-[N-(5-carboxyvaleryl)-glycyl]-amino-2-deoxy-β-D-glucopyranosyl}-N-octadecyl-dodecanamide,
N-{2-[N-(5-carboxyvaleryl)-glycyl]-amino-2-deoxy-β-D-glucopyranosyl} -N-octadecyl-octadecanamide,
N-{2-[N-(7-carboxyheptanoyl)-glycyl]-amino-2-deoxy-β-D-glucopyranosyl}-N-dodecyl-octadecanamide,
N-{2-[N-(7-carboxyheptanoyl)-glycyl]-amino-2-deoxy-β-D-glucopyranosyl}-N-tetradecyl-octadecanamide,
N-{2-[N-(7-carboxyheptanoyl)-glycyl]-amino-2-deoxy-β-D-glucopyranosyl}-N-octadecyl-dodecanamide,
N-{2-[N-(7-carboxyheptanoyl)-glycyl]-amino-2-deoxy-β-D-glucopyranosyl}-N-octadecyl-octadecanamide,
N-{2-[N-(3-carboxypropionyl)-L-alanyl]-amino-2-deoxy-β-D-glucopyranosyl}-N-dodecyl-octadecanamide,
N-{2-[N-(3-carboxypropionyl)-L-alanyl]-amino-2-deoxy-β-D-glucopyranosyl}-N-tetradecyl-octadecanamide,
N-{2-[N-(3-carboxypropionyl)-L-alanyl]-amino-2-deoxy-β-D-glucopyranosyl}-N-octadecyl-dodecanamide,
N-{2-[N-(3-carboxypropionyl)-L-alanyl]-amino-2-deoxy-β-D-glucopyranosyl}-N-octadecyl-octadecanamide,
N-{2-[N-(4-carboxybutyryl)-L-alanyl]-amino-2-deoxy-β-D-glucopyranosyl}-N-dodecyl-octadecanamide,
N-{2-[N-(4-carboxybutyryl)-L-alanyl]-amino-2-deoxy-β-D-glucopyranosyl}-N-tetradecyl-octadecanamide,
N-{2-[N-(4-carboxybutyryl)-L-alanyl]-amino-2-deoxy-β-D-glucopyranosyl}-N-octadecyl-dodecanamide,
N-{2-[N-(4-carboxybutyryl)-L-alanyl]-amino-2-deoxy-β-D-glucopyranosyl}-N-octadecyl-octadecanamide,
N-{2-[N-(5-carboxyvaleryl)-L-alanyl]-amino-2-deoxy-β-D-glucopyranosyl}-N-dodecyl-octadecanamide,
N-{2-[N-(5-carboxyvaleryl)-L-alanyl]-amino-2-deoxy-β-D-glucopyranosyl}-N-tetradecyl-octadecanamide,
N-{2-[N-(5-carboxyvaleryl)-L-alanyl]-amino-2-deoxy-β-D-glucopyranosyl}-N-octadecyl-dodecanamide,
N-{2-[N-(5-carboxyvaleryl)-L-alanyl]-amino-2-deoxy-β-D-glucopyranosyl}-N-octadecyl-octadecanamide,
N-{2-[N-(8-carboxyheptanoyl)-L-alanyl]-amino-2-deoxy-β-D-glucopyranosyl}-N-dodecyl-octadecanamide,
N-{2-[N-(8-carboxyheptanoyl)-L-alanyl]-amino-2-deoxy-β-D-glucopyranosyl}-N-tetradecyl-octadecanamide,
N-{2-[N-(8-carboxyheptanoyl)-L-alanyl]-amino-2-deoxy-β-D-glucopyranosyl} -N-octadecyl-dodecanamide,
N-{2-[N-(8-carboxyheptanoyl)-L-alanyl]-amino-2-deoxy-β-D-glucopyranosyl}-N-octadecyl-octadecanamide,
N-{2-[N-(3-carboxypropionyl)-L-leucyl]-amino-2-deoxy-β-D-glucopyranosyl}-N-dodecyl-dodecanamide,
N-{2-[N-(3-carboxypropionyl)-L-leucyl]-amino-2-deoxy-β-D-glucopyranosyl}-N-dodecyl-tetradecanamide,
N-{2-[N-(3-carboxypropionyl)-L-leucyl]-amino-2-deoxy-β-D-glucopyranosyl}-N-dodecyl-octadecanamide,
N-{2-[N-(3-carboxypropionyl)-L-leucyl]-amino-2-deoxy-β-D-glucopyranosyl}-N-tetradecyl-dodecanamide,
N-{2-[N-(3-carboxypropionyl)-L-leucyl]-amino-2-deoxy-β-D-glucopyranosyl}-N-tetradecyl-tetradecanamide,
N-{2-[N-(3-carboxypropionyl)-L-leucyl]-amino-2-deoxy-β-D-glucopyranosyl}-N-tetradecyl-octadecanamide,
N-{2-[N-(3-carboxypropionyl)-L-leucyl]-amino-2-deoxy-β-D-glucopyranosyl}-N-octadecyl-dodecanamide,
N-{2-[(3-carboxypropionyl)-L-leucyl]-amino-2-deoxy-β-D-glucopyranosyl}-N-octadecyl-tetradecanamide,
N-{2-[N-(3-carboxypropionyl)-L-leucyl]-amino-2-deoxy-β-D-glucopyranosyl}-N-octadecyl-octadecanamide,
N-{2-[N-(4-carboxybutyryl)-L-leucyl]-amino-2-deoxy-β-D-glucopyranosyl}-N-dodecyl-octadecanamide,
N-{2-[N-(4-carboxybutyryl)-L-leucyl]-amino-2-deoxy-β-D-glucopyranosyl}-N-tetradecyl-octadecanamide,
N-{2-[N-(4-carboxybutyryl)-L-leucyl]-amino-2-deoxy-β-D-glucopyranosyl}-N-octadecyl-dodecanamide,
N-{2-[N-(4-carboxybutyryl)-L-leucyl]-amino-2-deoxy-β-D-glucopyranosyl}-N-octadecyl-octadecanamide, N-{2-[N-(5-carboxyvaleryl)-L-leucyl]-amino-2-deoxy-β-D-glucopyranosyl}-N-dodecyl-octadecanamide,
N-{2-[N-(5-carboxyvaleryl)-L-leucyl]-amino-2-deoxy-β-D-glucopyranosyl}-N-tetradecyl-octadecanamide,
N-{2-[N-(5-carboxyvaleryl)-L-leucyl]-amino-2-deoxy-β-D-glucopyranosyl}-N-octadecyl-dodecanamide,
N-{2-[N-(5-carboxyvaleryl)-L-leucyl]-amino-2-deoxy-β-D-glucopyranosyl}-N-octadecyl-octadecanamide,
N-{2-[N-(7-carboxyheptanoyl)-L-leucyl]-amino-2-deoxy-β-D-glucopyranosyl}-N-dodecyl-octadecanamide,
N-{2-[N-(7-carboxyheptanoyl)-L-leucyl]-amino-2-deoxy-β-D-glucopyranosyl}-N-tetradecyl-octadecanamide,
N-{2-[N-(7-carboxyheptanoyl)-L-leucyl]-amino-2-deoxy-β-D-glucopyranosyl}-N-octadecyl-dodecanamide,
N-{2-[N-(7-carboxyheptanoyl)-L-leucyl]-amino-2-deoxy-β-D-glucopyranosyl}-N-octadecyl-octadecanamide,
N-{2-[N-(3-carboxypropionyl)-L-seryl]-amino-2-deoxy-β-D-glucopyranosyl}-N-dodecyl-octadecanamide,
N-{2-[N-(3-carboxypropionyl)-L-seryl]-amino-2-deoxy-β-D-glucopyranosyl}-N-tetradecyl-octadecanamide,
N-{2-[N-(carboxypropionyl)-L-seryl]-amino-2-deoxy-β-D-glucopyranosyl}-N-octadecyl-dodecanamide,
N-{2-[N-(3-carboxypropionyl)-L-seryl]-amino-2-deoxy-β-D-glucopyranosyl}-N-octadecyl-octadecanamide,
N-{2-[N-(4-carboxybutyryl)-L-seryl]-amino-2-deoxy-β-D-glucopyranosyl}-N-dodecyl-octadecanamide,
N-{2-[N-(4-carboxybutyryl)-L-seryl]-amino-2-deoxy-β-D-glucopyranosyl}-N-tetradecyl-octadecanamide,
N-{2-[N-(4-carboxybutyryl)-L-seryl]-amino-2-deoxy-β-D-glucopyranosyl}-N-octadecyl-dodecanamide,
N-{2-[N-(4-carboxybutyryl)-L-seryl]-amino-2-deoxy-β-D-glucopyranosyl}-N-octadecyl-octadecanamide,
N-{2-[N-(5-carboxyvaleryl)-L-seryl]-amino-2-deoxy-β-D-glucopyranosyl}-N-dodecyl-octadecanamide,
N-{2-[N-(5-carboxyvaleryl)-L-seryl]-amino-2-deoxy-β-D-glucopyranosyl}-N-tetradecyl-octadecanamide,
N-{2-[N-(5-carboxyvaleryl)-L-seryl]-amino-2-deoxy-β-D-glucopyranosyl}-N-octadecyl-dodecanamide,
N-{2-[N-(5-carboxyvaleryl)-L-seryl]-amino-2-deoxy-β-D-glucopyranosyl}-N-octadecyl-octadecanamide,
N-{2-[N-(7-carboxyheptanoyl)-L-seryl]-amino-2-deoxy-β-D-glucopyranosyl}-N-dodecyl-octadecanamide,
N-{2-[N-(7-carboxyheptanoyl)-L-seryl]-amino-2-deoxy-β-D-glucopyranosyl}-N-tetradecyl-octadecanamide,
N-{2-[N-(7-carboxyheptanoyl)-L-seryl]-amino-2-deoxy-β-D-glucopyranosyl}-N-octadecyl-dodecanamide,
N-{2-[N-(7-carboxyheptanoyl)-L-seryl]-amino-2-deoxy-β-D-glucopyranosyl}-N-octadecyl-octadecanamide,
N-{2-[N-(3-carboxypropionyl)-L-phenylalanyl]-amino-2-deoxy-β-D-glucopyranosyl}-N-dodecyl-octadecanamide,
N-{2-[N-(3-carboxypropionyl)-L-phenylalanyl]-amino-2-deoxy-β-D-glucopyranosyl}-N-tetradecyl-octadecanamide,
N-{2-[N-(3-carboxypropionyl)-L-phenylalanyl]-amino-2-deoxy-β-D-glucopyranosyl}-N-octadecyl-dodecanamide,
N-{2-[N-(3-carboxypropionyl)-L-phenylalanyl]-amino-2-deoxy-β-D-glucopyranosyl}-N-octadecyl-octadecanamide,
N-{2-[N-(4-carboxybutyryl)-L-phenylalanyl]-amino-2-deoxy-β-D-glucopyranosyl}-N-dodecyl-octadecanamide,
N-{2-[N-(4-carboxybutyryl)-L-phenylalanyl]-amino-2-deoxy-β-D-glucopyranosyl}-N-tetradecyl-octadecanamide,
N-{2-[N-(4-carboxybutyryl)-L-phenylalanyl]-amino-2-deoxy-β-D-glucopyranosyl}-N-octyl-dodecanamide,
N-{2-[N-(4-carboxybutyryl)-L-phenylalanyl]-amino-2-deoxy-β-D-glucopyranosyl}-N-octadecyl-octadecanamide,
N-{2-[N-(5-carboxyvaleryl)-L-phenylalanyl]-amino-2-deoxy-β-D-glucopyranosyl}-N-dodecyl-octadecanamide,
N-{2-[N-(5-carboxyvaleryl)-L-phenylalanyl]-amino-2-deoxy-β-D-glucopyranosyl}-N-tetradecyl-octadecanamide,
N-{2-[N-(5-carboxyvaleryl)-L-phenylalanyl]-amino-2-deoxy-β-D-glucopyranosyl}-N-octadecyl-dodecanamide,
N-{2-[N-(5-carboxyvaleryl)-L-phenylalanyl]-amino-2-deoxy-β-D-glucopyranosyl}-N-octadecyl-octadecanamide,
N-{2-[N-(7-carboxyheptanoyl)-L-phenylalanyl]-amino-2-deoxy-β-D-glucopyranosyl}-N-dodecyl-octadecanamide,
N-{2-[N-(7-carboxyheptanoyl)-L-phenylalanyl]-amino-2-deoxy-β-D-glucopyranosyl}-N-tetradecyl-octadecanamide,
N-{2-[N-(7-carboxyheptanoyl)-L-phenylalanyl]-amino-2-deoxy-β-D-glucopyranosyl}-N-octadecyl-dodecanamide,
N-{2-[N-(7-carboxyheptanoyl)-L-phenylalanyl]-amino-2-deoxy-β-D-glucopyranosyl}-N-octadecyl-octadecanamide,
N-[2-(3-carboxypropionylamino)-2-deoxy-β-D-galactopyranosyl]-N-dodecyl-dodecanamide,
N-[2-(3-carboxypropionylamino)-2-deoxy-β-D-galactopyranosyl]-N-dodecyl-tetradecanamide,
N-[2-(3-carboxypropionylamino)-2-deoxy-β-D-galactopyranosyl]-N-dodecyl-octadecanamide,
N-[2-(3-carboxypropionylamino)-2-deoxy-β-D-galactopyranosyl]-N-tetradecyl-dodecanamide,
N-[2-(3-carboxypropionylamino)-2-deoxy-β-D-galactopyranosyl]-N-tetradecyl-tetradecanamide,
N-[2-(3-carboxypropionylamino)-2-deoxy-β-D-galactopyranosyl]-N-tetradecyl-octadecanamide,
N-[2-(3-carboxypropionylamino)-2-deoxy-β-D-galactopyranosyl]-N-octadecyl-dodecanamide,
N-[2-(3-carboxypropionylamino)-2-deoxy-β-D-galactopyranosyl]-N-octadecyl-tetradecanamide,
N-[2-(3-carboxypropionylamino)-2-deoxy-β-D-galactopyranosyl]-N-octadecyl-octadecanamide,
N-[2-(4-carboxybutyrylamino)-2-deoxy-β-D-galactopyranosyl]-N-dodecyloctadecanamide,
N-[2-(4-carboxybutyrylamino)-2-deoxy-β-D-galactopyranosyl]-N-tetradecyl-octadecanamide,
N-[2-(4-carboxybutyrylamino)-2-deoxy-β-D-galactopyranosyl]-N-octadecyl-dodecanamide,
N-[2-(4-carboxybutyrylamino)-2-deoxy-β-D-galactopyranosyl]-N-octadecyl-octadecanamide,
N-[2-5-carboxyvalerylamino)-2-deoxy-β-D-galactopyranosyl]-N-dodecyl-octadecanamide,
N-[2-5-carboxyvalerylamino)-2-deoxy-β-D-galactopyranosyl]-N-tetradecyl-octadecanamide, N-[2-5-carboxyvalerylamino)-2-deoxy-β-D-galac-
topyranosyl]-N-octadecyl-dodecanamide,
N-[2-5-carboxyvalerylamino)-2-deoxy-β-D-galac-
topyranosyl]-N-octadecyl-octadecanamide,
N-[2-(7-carboxyheptanoylamino)-2-deoxy-β-D-galac-
topyranosyl]-N-dodecyl-octadecanamide,
N-[2-(7-carboxyheptanoylamino)-2-deoxy-β-D-galac-
topyranosyl]-N-tetradecyl-octadecanamide,
N-[2-(7-carboxyheptanoylamino)-2-deoxy-β-D-galac-
topyranosyl]-N-octadecyl-dodecanamide,
N-[2-(7-carboxyheptanoylamino)-2-deoxy-β-D-galac-
topyranosyl]-N-octadecyl-octadecanamide,
N-{2-[N-(3-carboxypropionyl)-glycyl]-amino-2-deoxy-
β-D-galactopyranosyl} -N-dodecyl-dodecanamide,
N-{2-[N-(3-carboxypropionyl)-glycyl]-amino-2-deoxy-
β-D-galactopyranosyl}-N-dodecyl-tetradecanamide,
N-{2-[N-(3-carboxypropionyl)-glycyl]-amino-2-deoxy-
β-D-galactopyranosyl}-N-dodecyl-octadecanamide,
N-{2-[N-(3-carboxypropionyl)-glycyl]-amino-2-deoxy-
β-D-galactopyranosyl}-N-tetradecyl-dodecanamide,
N-{2-[N-(3-carboxypropionyl)-glycyl]-amino-2-deoxy-
β-D-galactopyranosyl}-N-tetradecyl-tetradecana-
mide,
N-{2-[N-(3-carboxypropionyl)-glycyl]-amino-2-deoxy-
β-D-galactopyranosyl}-N-tetradecyl-octadecana-
mide,
N-{2-[N-(3-carboxypropionyl)-glycyl]-amino-2-deoxy-
β-D-galactopyranosyl}-N-octadecyl-dodecanamide,
N-{2-[N-(3-carboxypropionyl)-glycyl]-amino-2-deoxy-
β-D-galactopyranosyl}-N-octadecyl-tetradecana-
mide and
N-{2-[N-(3-carboxypropionyl)-glycyl]-amino-2-deoxy-
β-D-galactopyranosyl}-N-octadecyl-octadecana-
mide.

7. A process for the preparation of a compound according to claim 1, wherein a glycosylamide of the formula

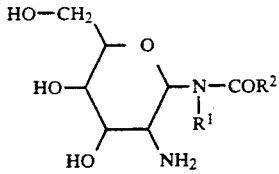

or a peptidoglycolipid of the formula

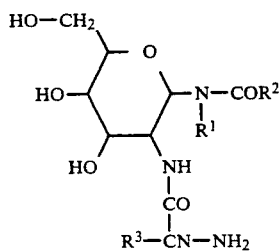

is reacted with an activated dicarboxylic acid derivative or with a non-activated dicarboxylic acid derivative in the presence of a condensing agent.

8. A pharmaceutical composition useful to stimulate intrinsic defenses and non-specific defenses of a host to which it is administered comprising an effective amount thereof of at least one compound according to claim 1 and a pharmaceutically acceptable diluent.

9. A methd of stimulating the intrinsic defenses and non-specific defenses of a host comprising administering to said host an effective amount of at least one compound according to claim 1.

* * * * *

UNITED STATES PATENT AND TRADEMARK OFFICE
CERTIFICATE OF CORRECTION

PATENT NO. : 5,070,190

DATED : December 3, 1991

INVENTOR(S) : Lockhoff et al.

It is certified that error appears in the above-identified patent and that said Letters Patent is hereby corrected as shown below:

| | |
|---|---|
| Title Page | U.S. PATENT DOCUMENTS: After " 4,699,899, 10/1987 " delete " KLruger " and substitute -- Kruger -- |
| Col. 18, line 64 | After " -N- " delete " tetradecyl " and substitute -- dodecyl -- |
| Col. 19, line 43 | Delete " glycopyranosyl " and substitute -- glucopyranosyl -- |
| Col. 22, line 58 | After " dodecyl " insert -- - -- |

Signed and Sealed this

Seventh Day of December, 1993

*Attest:*

BRUCE LEHMAN

*Attesting Officer*     *Commissioner of Patents and Trademarks*